US009608580B2

(12) United States Patent
Ko et al.

(10) Patent No.: US 9,608,580 B2
(45) Date of Patent: Mar. 28, 2017

(54) BIOSIGNAL AMPLIFYING CIRCUIT

(71) Applicants: SAMSUNG ELECTRONICS CO., LTD., Suwon-si (KR); The Industry & Academic Cooperation in Chungnam National University (IAC), Daejeon (KR)

(72) Inventors: Hyoung Ho Ko, Daejeon (KR); Jong Pal Kim, Seoul (KR); Tak Hyung Lee, Suwon-si (KR)

(73) Assignees: Samsung Electronics Co., Ltd., Suwon-si (KR); The Industry & Academic Cooperation in Chungnam National University (IAC), Daejeon (KR)

( * ) Notice: Subject to any disclaimer, the term of this patent is extended or adjusted under 35 U.S.C. 154(b) by 33 days.

(21) Appl. No.: 14/594,480

(22) Filed: Jan. 12, 2015

(65) Prior Publication Data

US 2015/0200637 A1  Jul. 16, 2015

(30) Foreign Application Priority Data

Jan. 13, 2014  (KR) .................... 10-2014-0004037

(51) Int. Cl.
| | | |
|---|---|---|
| H03F 1/02 | (2006.01) | |
| H03F 3/72 | (2006.01) | |
| A61B 5/04 | (2006.01) | |
| A61B 5/0428 | (2006.01) | |
| H03F 3/393 | (2006.01) | |

(Continued)

(52) U.S. Cl.
CPC .......... *H03F 3/72* (2013.01); *A61B 5/04004* (2013.01); *A61B 5/0428* (2013.01);
(Continued)

(58) Field of Classification Search
CPC ..................................... H03F 1/02; H03F 3/38
(Continued)

(56) References Cited

U.S. PATENT DOCUMENTS 4,298,843 A * 11/1981 Nixon ..................... H03F 1/303
330/69
7,589,587 B2 * 9/2009 Yoshida .................. H03F 3/387
330/258
(Continued)

FOREIGN PATENT DOCUMENTS

CN           101278838 A    10/2008
KR    10-2009-0104903 A    10/2009
(Continued)

OTHER PUBLICATIONS

Helleputte, N. et al., "160 µA Biopotential Acquisition IC With Fully Integrated IA and Motion Artifact Suppression," IEEE Transactions on Biomedical Circuits and Systems, vol. 6, No. 6, Dec. 2012 (10 pages).

(Continued)

*Primary Examiner* — Henry Choe
(74) *Attorney, Agent, or Firm* — NSIP Law

(57) ABSTRACT

A biosignal apparatus is described including an amplifier and a sampler. The amplifier is configured to alternate between an operating state and a low power state based on a periodically changing control signal. The sampler is configured to sample a signal output from the amplifier in response to the amplifier being in the operating state and maintain the sampled signal in response to the amplifier being in the low power state.

17 Claims, 23 Drawing Sheets

(51) Int. Cl.
 *A61B 5/00* (2006.01)
 *H03K 17/687* (2006.01)
 *H03F 3/45* (2006.01)

(52) U.S. Cl.
 CPC .......... *A61B 5/7225* (2013.01); *H03F 1/0277* (2013.01); *H03F 3/393* (2013.01); *H03F 3/45475* (2013.01); *H03K 17/687* (2013.01); *A61B 2560/0209* (2013.01); *H03F 2200/261* (2013.01); *H03F 2200/333* (2013.01); *H03F 2203/7227* (2013.01)

(58) Field of Classification Search
 USPC .................................................. 330/9, 10, 51
 See application file for complete search history.

(56) References Cited

U.S. PATENT DOCUMENTS

| 8,120,422 | B1 | 2/2012 | Huijsing et al. |
| 8,466,742 | B2 | 6/2013 | Yazicioglu et al. |
| 2003/0069486 | A1 | 4/2003 | Sueppel et al. |
| 2005/0275460 | A1 | 12/2005 | Botker |
| 2007/0260150 | A1 | 11/2007 | Chow et al. |
| 2009/0128232 | A1* | 5/2009 | Deng .................. H03F 3/005 330/9 |
| 2010/0289568 | A1 | 11/2010 | Eschauzier et al. |
| 2011/0066054 | A1 | 3/2011 | Yazicioglu et al. |
| 2012/0188009 | A1 | 7/2012 | Alexander et al. |
| 2013/0303942 | A1 | 11/2013 | Damaser et al. |

FOREIGN PATENT DOCUMENTS

| KR | 10-2009-0104908 A | 10/2009 |
| KR | 10-2012-0089410 A | 8/2012 |
| WO | WO 2013/123359 A2 | 8/2013 |

OTHER PUBLICATIONS

Partial European Search Report issued on Jun. 9, 2015 in counterpart European Application No. 14190823.6 (7 pages).

* cited by examiner

BIOSIGNAL AMPLIFYING CIRCUIT

CROSS-REFERENCE TO RELATED APPLICATION(S)

This application claims the benefit under 35 USC 119(a) of Korean Patent Application No. 10-2014-0004037, filed on Jan. 13, 2014, in the Korean Intellectual Property Office, the entire disclosure of which is incorporated herein by reference for all purposes.

BACKGROUND

1. Field

The following description relates to a biosignal amplifying circuit, and more particularly, to technology for amplifying various biosignals, for example, an electrocardiogram (ECG), an electromyogram (EMG), an electrooculogram (EOG), and a brainwave, measured from a human body.

2. Description of Related Art

Various medical devices used to diagnose health conditions of a patient are under development. In particular, particular attention is being given to medical devices that measure an electrical biosignal of the patient for patient convenience during a diagnostic process and prompt delivery of diagnostic results.

A biopotential is generated by an electric field formed in a human body and measured to be a voltage of a portion based on an electric field intensity. A source of the biopotential may be an excitable cell reacting to an application of electrical stimulation and exhibiting electric excitation. The excitable cell induces an action potential based on the electric excitation, and the action potential induced by the excitable cell is transmitted through a nerve fiber. The electric field is formed in the body due to the action potential.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an illustrative example, there is provided a biosignal apparatus, including an amplifier configured to alternate between an operating state and a low power state based on a periodically changing control signal; and a sampler configured to sample a signal output from the amplifier in response to the amplifier being in the operating state and maintain the sampled signal in response to the amplifier being in the low power state.

The apparatus may also include a selector configured to select a bias voltage corresponding to the operating mode, wherein the amplifier may include switches to be reconfigured based on an operating point corresponding to the operating mode.

Each of the switches may include transistors sharing a source and a drain, wherein the transistors may be configured to receive an identical gate signal at a first operating point, and wherein at least a part of the transistors may be configured to receive a gate signal that turns off the part of the transistors at a second operating point.

The amplifier may include a switch including transistors to be alternately turned on and off.

The switch may include two transistors sharing a source and a drain, wherein, at a first timing, a gate of a first transistor is configured to receive a gate signal and a second transistor may be configured to be turned off, and wherein, at a second timing, a gate of the second transistor may be configured to receive the gate signal and the first transistor is turned off.

The amplifier may be configured to receive an enable signal and receive a bias voltage to amplify an input signal in response to the enable signal having a logic value corresponding to the operating state, and wherein a period length of the enable signal may be greater by a factor of a period length of the control signal.

The sampler may be disposed at an input terminal of a direct current servo loop (DSL) circuit.

The sampler may be disposed at an input terminal of a bootstrap circuit.

The amplifier may further include a transconductance (TC) input terminal configured to convert and amplify a modulated input voltage to a current; and a transimpedance (TI) output terminal configured to convert and amplify a current to an output voltage.

The apparatus may further include a timing generator configured to generate an enable signal (EN) that turns on or off a current source of the TC input terminal and the TI output terminal based on an operating timing of a chopper stabilization device, and configured to sample the output voltage.

The selector may select a bias current source by multiplexing a current source and a voltage source to reconfigure an amount of power consumption.

In accordance with another illustrative configuration, there is provided an apparatus including a switch configured to be reconfigured based on an operating point of an operating mode; and a selector configured to select a bias voltage corresponding to the operating mode.

A width and a length of the switch may be reconfigured based on the operating point.

The switch may include transistors sharing a source and a drain, wherein, at a first operating point, the transistors may be configured to receive an identical gate signal, and wherein, at a second operating point, at least a part of the transistors may be configured to receive a gate signal that turns off the part of the transistors.

The operating mode may include a low power mode and a high quality mode.

Through static switching, the selector may select a bias current source by multiplexing a current source and a voltage source to reconfigure an amount of power consumption.

In accordance with an illustrative configuration, there is provided a biosignal apparatus, including a switch including transistors; and a controller configured to control the switch to enable the transistors to be alternately turned on and off.

The switch may include two transistors sharing a source and a drain, wherein, at a first timing, a gate of a first transistor may be configured to receive a gate signal and a second transistor may be configured to be turned off, and wherein, at a second timing, a gate of the second transistor may be configured to receive the gate signal and the first transistor is turned off.

The switch may be disposed at an input terminal of the biosignal apparatus.

The apparatus may also include a modulator configured to modulate an input signal to a high frequency; and a demodulator configured to demodulate the modulated signal.

An edge of a clock operating a chopper in the modulator and a chopper in the demodulator and an edge of a clock operating the switching circuit may be periodically synchronized.

Other features and aspects will be apparent from the following detailed description, the drawings, and the claims.

BRIEF DESCRIPTION OF THE DRAWINGS

These and/or other aspects will become apparent and more readily appreciated from the following description of the embodiments, taken in conjunction with the accompanying drawings in which.

Figure 1A:
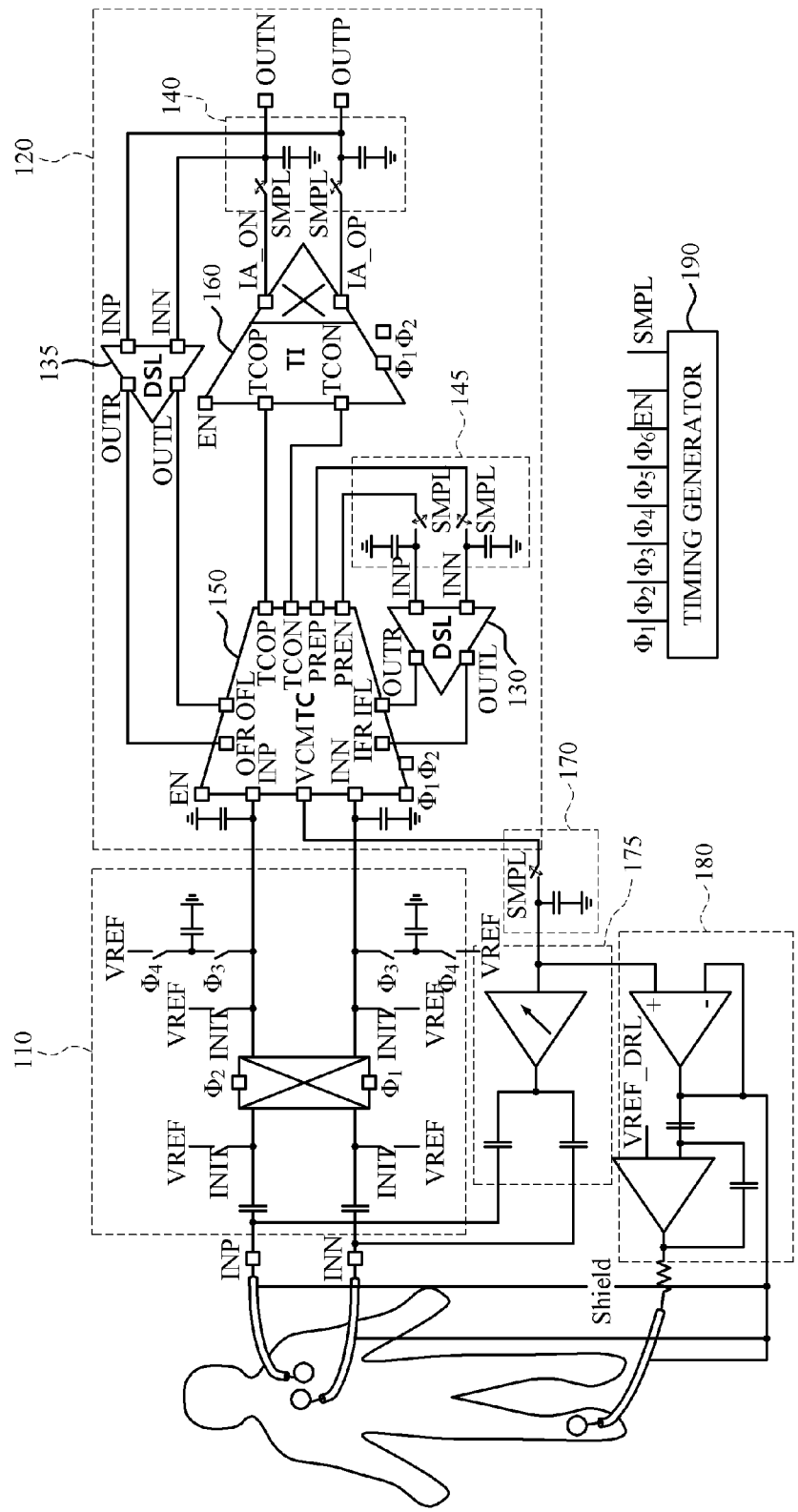
FIG. 1A is a diagram illustrating an example of a biosignal amplifying circuit, in accordance with an embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Overview of a Biosignal Amplifying Circuit

Figure 1B:
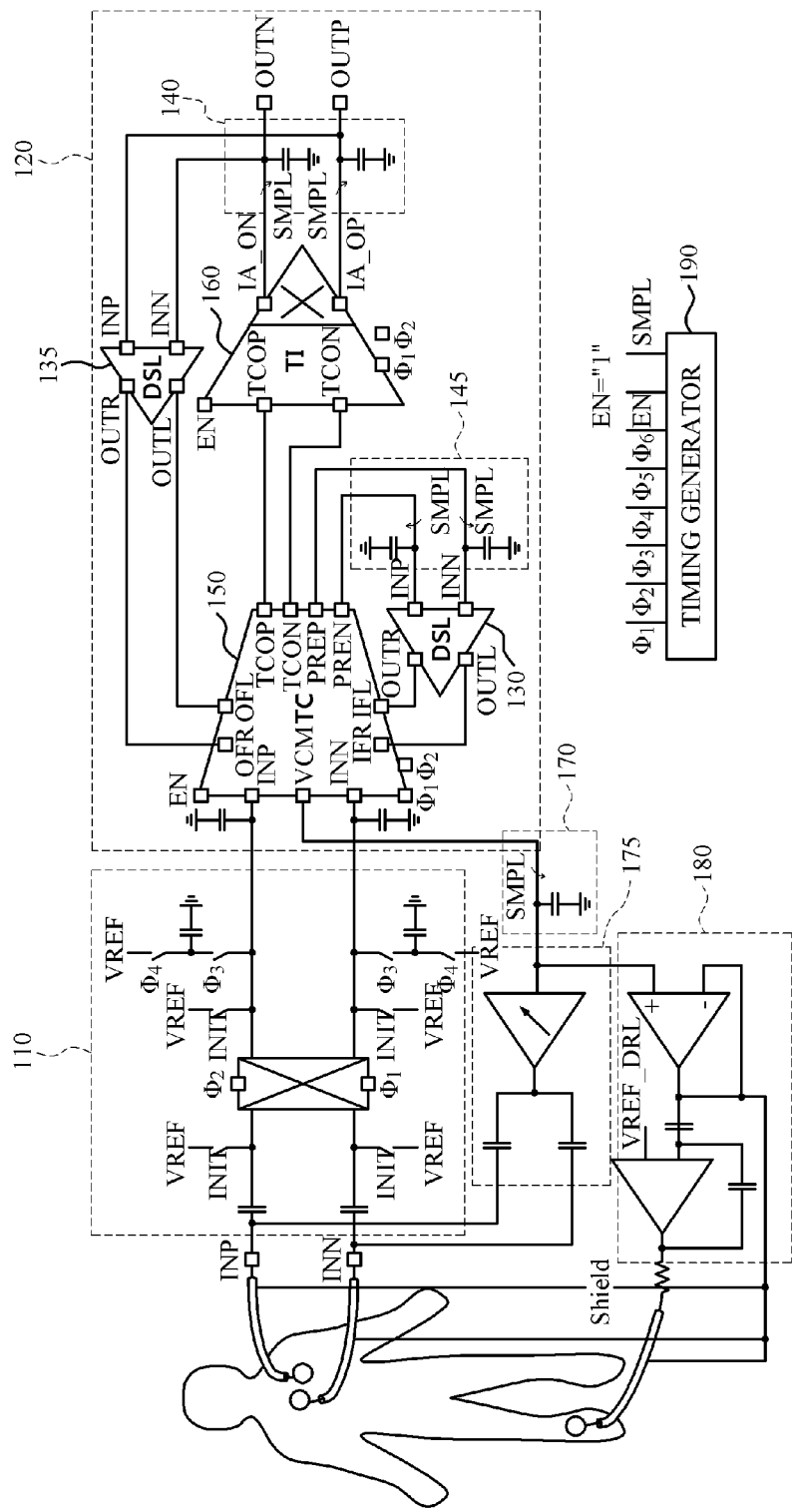
FIG. 1B is a diagram illustrating an example of a biosignal amplifying circuit, in accordance with an embodiment.
Figure 1C:
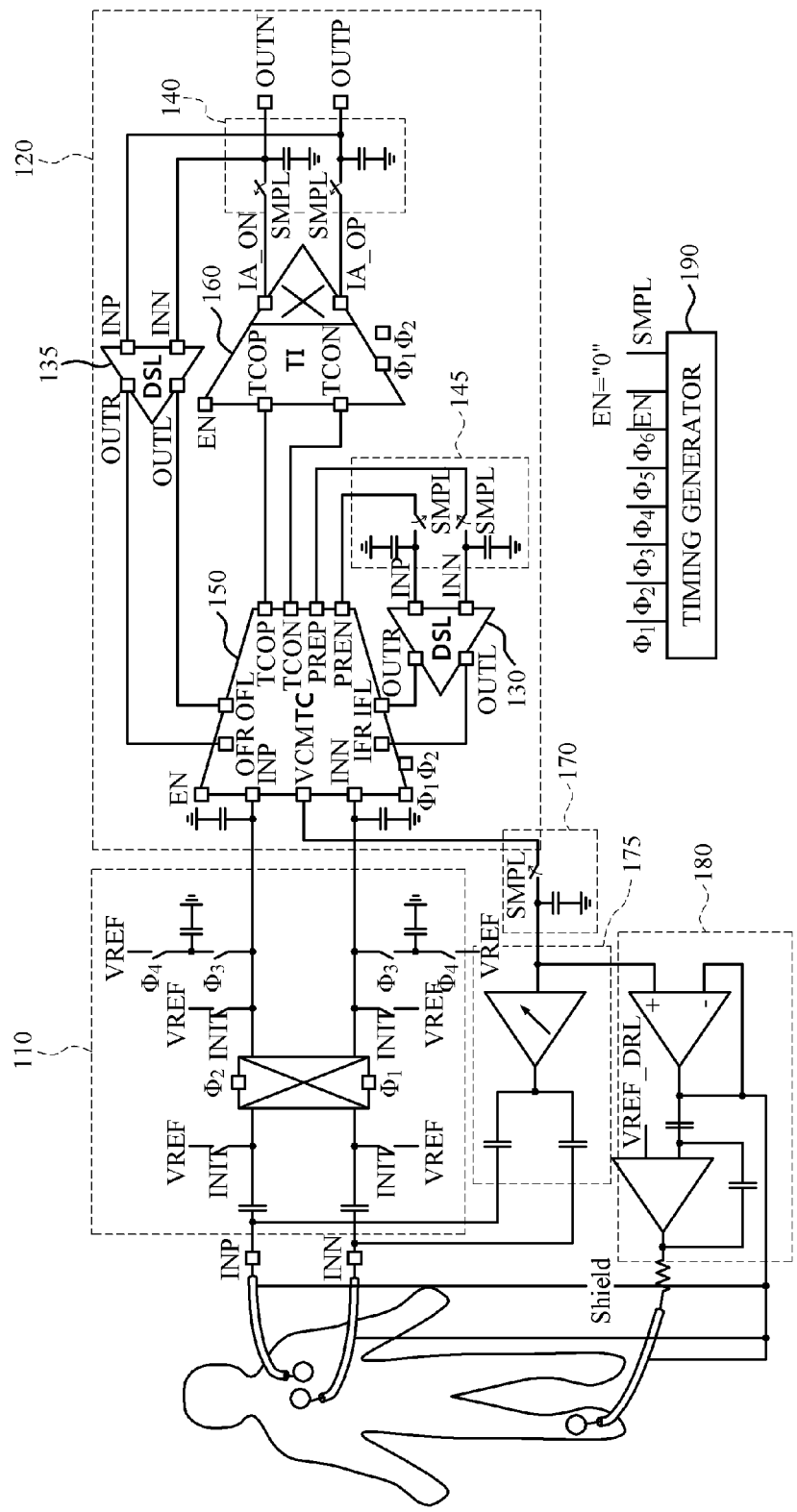
FIG. 1C is a diagram illustrating an example of a biosignal amplifying circuit, in accordance with an embodiment.

FIG. 1A-1C is a diagram illustrating an example of a biosignal amplifying circuit, in accordance with an embodiment. Referring to FIG. 1A, the biosignal amplifying circuit is configured to measure various forms of biosignals, for example, an electrocardiogram (ECG), and a brainwave.

Referring to FIG. 1A, the biosignal amplifying circuit includes an amplifier 120 to amplify a biosignal. The biosignal amplifying circuit further includes a modulator or modulation circuit 110 at a front terminal of the amplifier 120. Here, the biosignal is input through a terminal INP and a terminal INN of the modulation circuit 110. The biosignal is modulated to a high frequency as the biosignal passes through a capacitor of the modulation circuit 110, alternating current (AC) coupling, a chopper operating as a first frequency signal ($\Phi1$) and a second frequency signal ($\Phi2$).

The modulation circuit 110 uses a third frequency signal ($\Phi3$), a fourth frequency signal ($\Phi4$), and a capacitor to implement a switched capacitor resistance. The modulation circuit 110 also forms a direct current (DC) bias voltage of the terminal INP and the terminal INN of the amplifier 120 using the switched capacitor resistance.

The amplifier 120 amplifies the modulated biosignal to the high frequency. The amplifier 120 includes a transconductance (TC) input terminal 150 to convert and amplify a modulated input voltage to a current and a transimpedance (TI) output terminal 160 to convert and amplify a current to a voltage. Detailed configurations of the TC input terminal 150 and the TI output terminal 160 will be provided with reference to FIGS. 2 and 3.

Figure 2A:
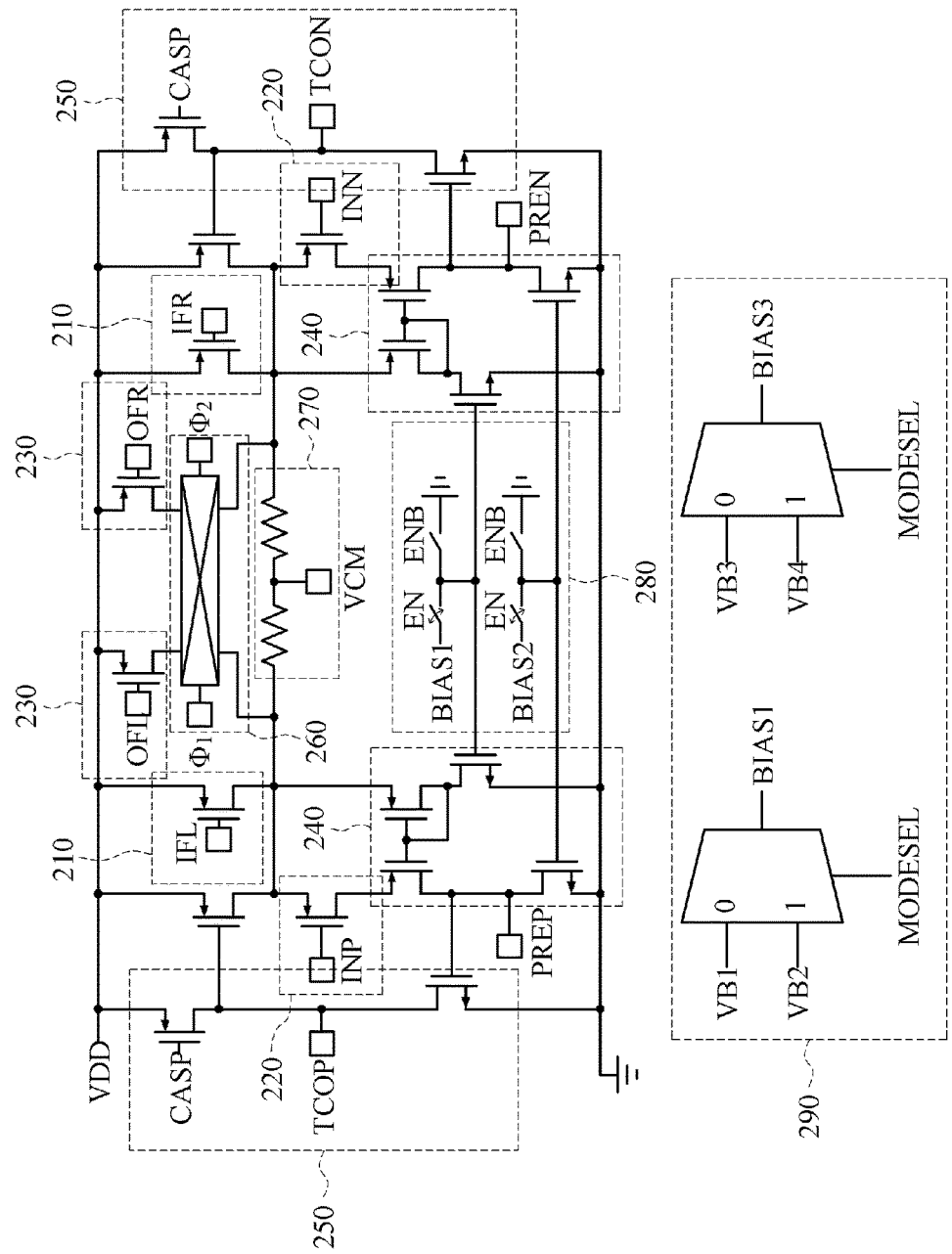
FIG. 2A is a diagram illustrating an example of a transconductance amplifying circuit, in accordance with an embodiment.
Figure 2B:
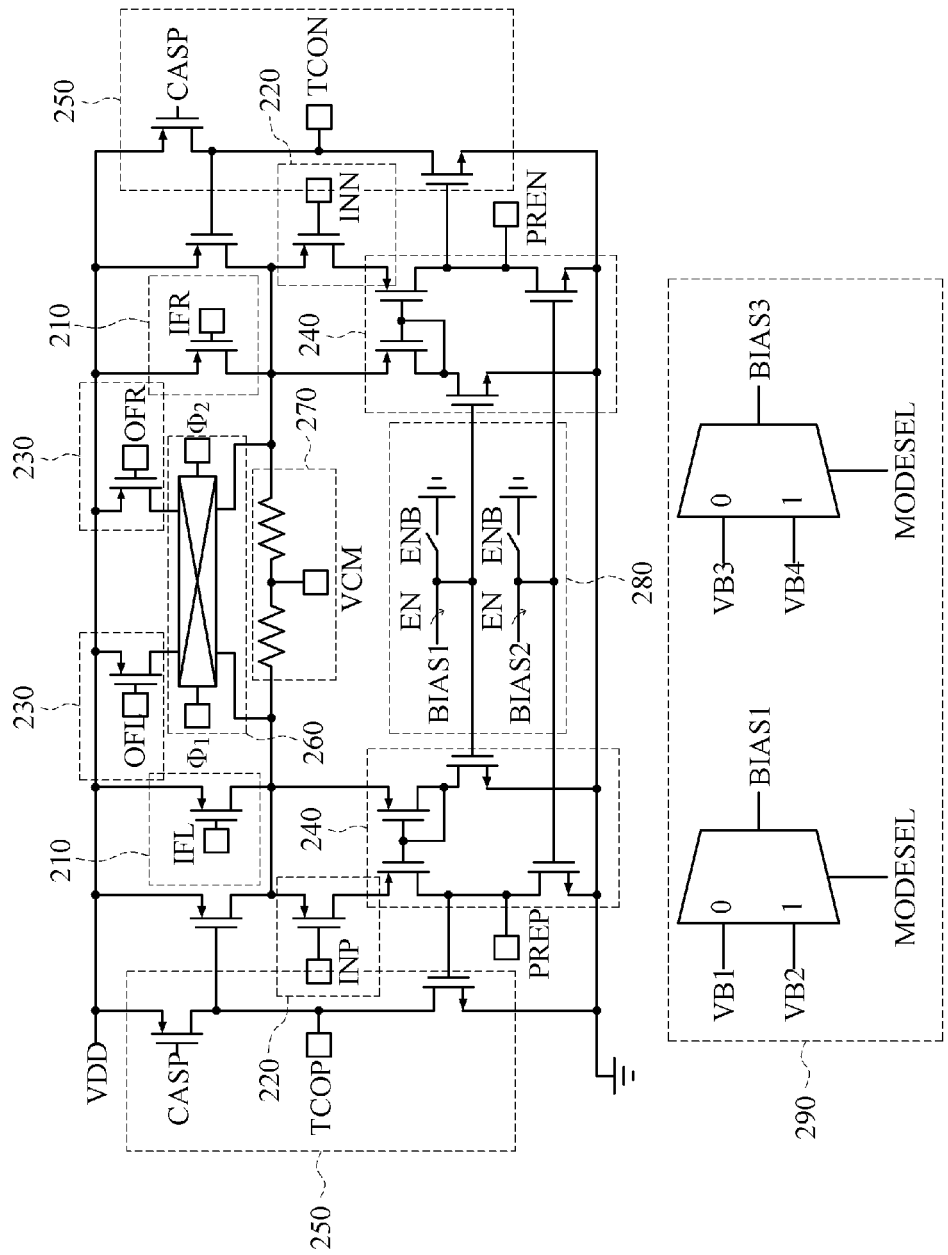
FIG. 2B is a diagram illustrating an example of a transconductance amplifying circuit, in accordance with an embodiment.

FIG. 2A-2B is a diagram illustrating an example of a transconductance amplifying circuit, in accordance with an embodiment. As an example, a detailed configuration of the transconductance (TC) input terminal 150 of FIG. 1A may be illustrated in FIG. 2A.

Referring to FIG. 2A, an input signal input through a gate of a transistor 220 may pass through a flipped voltage follower 240, and be first amplified and output to a terminal PREP and a terminal PREN. In one configuration, the input signal input through the gate of the transistor 220 is the biosignal modulated to a high frequency from the modulation circuit 110. The output signal output to the terminal PREP and the terminal PREN may be output by passing through a common source amplifier 250 and direct current (DC) level shifting to a terminal TCOP and a terminal TCON. A source terminal of the transistor 220 may be connected to a resistance 270. A medium voltage of the resistance 270 is output as a common mode voltage ($V_{CM}$).

The biosignal amplifying circuit of FIG. 1A may further include a DC servo loop (DSL) 130 and a DSL 135. To reduce a DC offset, an output voltage of the DSL 130 of FIG. 1A is fed back through a gate of a transistor 210. Also, an output voltage of the DSL 135 of FIG. 1A is fed back through a gate of a transistor 230 and modulated through a chopper 260 to eliminate a DC offset.

Figure 3:
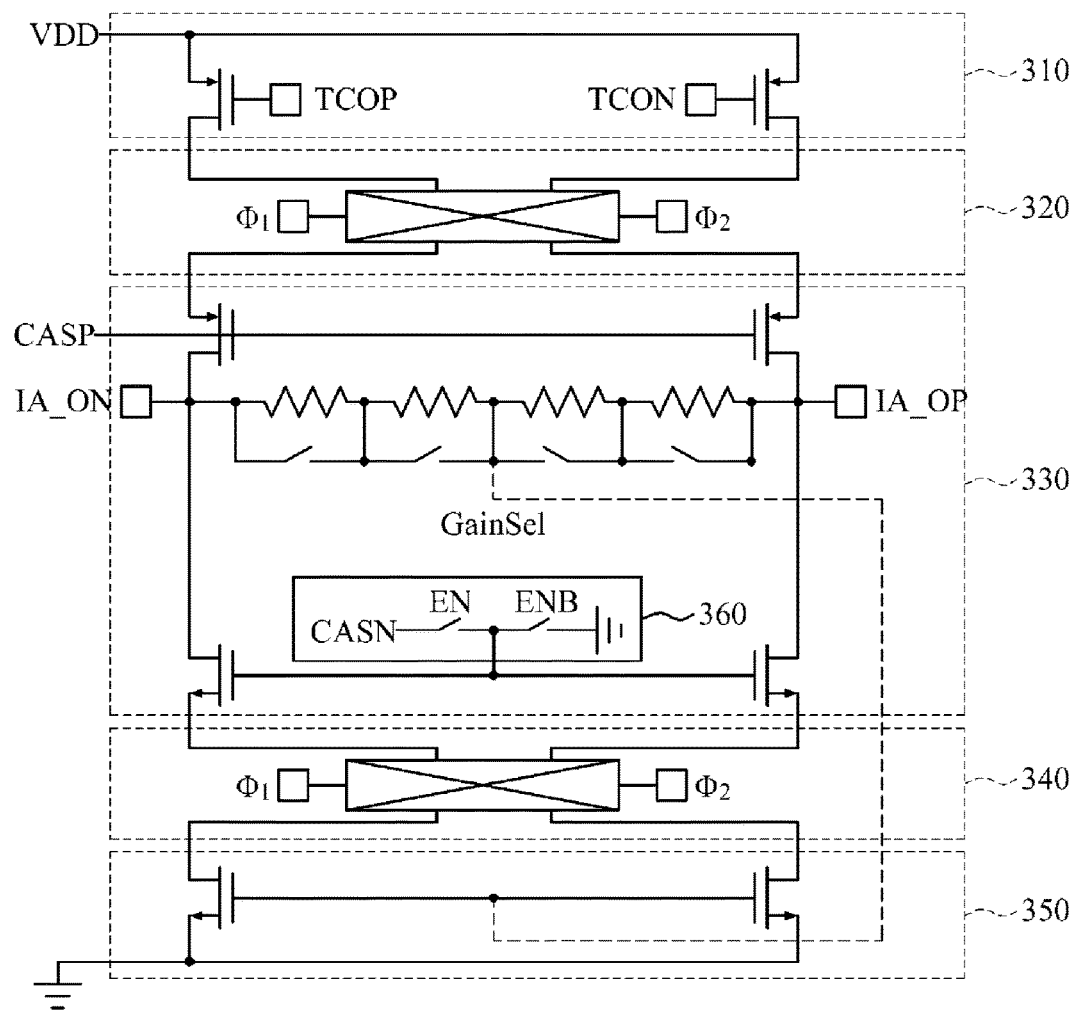
FIG. 3 is a diagram illustrating an example of a transimpedance amplifying circuit, in accordance with an embodiment.

FIG. 3 is a diagram illustrating an example of a transimpedance amplifying circuit, in accordance with an embodiment. As an example, a detailed configuration of the transimpedance (TI) output terminal 160 of FIG. 1A may be illustrated in FIG. 3.

Referring to FIG. 3, a gate of a transistor 310 receives an output signal of the TC input terminal 150 of FIG. 1A. When a signal modulated by the TC input terminal 150 is input to the gate of the transistor 310, a source-drain current of the transistor 310 is demodulated through a chopper 320 and a chopper 340. The demodulated signal is converted to a voltage through a resistance of a voltage converter 330. The resistance of the voltage converter 330 is configured to be programmable and; thus, an overall gain of the transimpedance amplifying circuit may be adjusted.

Figure 4:
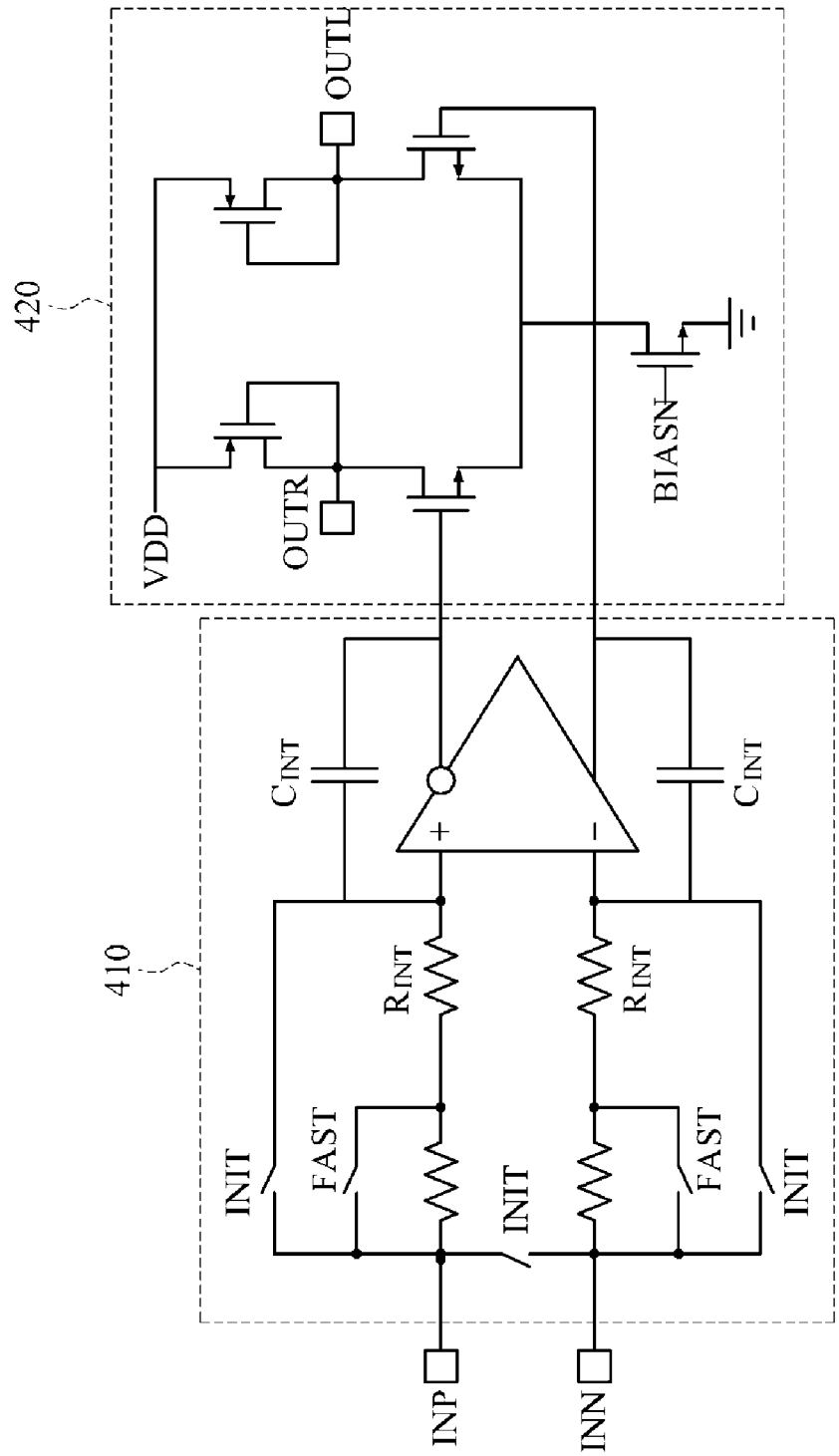
FIG. 4 is a diagram illustrating an example of a direct current servo loop (DSL) circuit, in accordance with an embodiment.

FIG. 4 is a diagram illustrating an example of a DSL circuit, in accordance with an embodiment. As an example, a detailed configuration of the DSL 130 and the DSL 135 of FIG. 1A may be illustrated in FIG. 4.

Referring to FIG. 4, an integrator 410 integrates a differential voltage input through a terminal INP and a terminal INN. The integrator 410 includes a resistance ($R_{INT}$), a feedback capacitor ($C_{INT}$), and a fully differential amplifier. A single level amplifier 420 amplifies an output voltage of the fully differential amplifier.

Static Switching

A biosignal amplifying circuit provides a flexible structure reconfigures a performance index, for example, power consumption, a gain, and a bandwidth, through static switching and dynamic switching.

For example, the biosignal amplifying circuit receives a mode selecting signal (MODESEL) corresponding to an operating mode. The operating mode may include a low power mode and a high quality mode. In the high quality mode, the biosignal amplifying circuit consumes a high current and outputs a high quality signal. In the low power mode, the biosignal amplifying circuit consumes a low current.

The biosignal amplifying circuit includes a selector or a selection circuit to select a bias voltage corresponding to the operating mode and switching circuits to be reconfigured based on an operating point corresponding to the operating mode. The selection circuit may select the bias voltage based on a current level corresponding to the operating mode. The switching circuits may be reconfigured based on the current level corresponding to the operating mode. As an example, the reconfiguration of the switching circuits indicates a reconfiguration of a width (W) and a length (L) of a MOS transistor.

Through the static switching, the biosignal amplifying circuit selects a bias current source by using a multiplexing scheme to reconfigure an amount of power consumption. The biosignal amplifying circuit reconfigures the W and the L of a transistor to allow the biosignal amplifying circuit to operate at an optimal operating point based on the bias current source.

Referring to FIG. 2A, the multiplexer 290 selects a bias voltage corresponding to a MODESEL. An operating point of a TC input terminal circuit may be changed based on the selected bias voltage. Transistors of FIG. 2A may be reconfigurable to operate at the changed operating point.

For example, the multiplexer 290 may select the bias voltage corresponding to a low power mode. When a transistor included in a flipped voltage follower 240 is provided in a reconfigurable form, a W/L ratio of the transistor included in the flipped voltage follower 240 may be reduced based on the selected bias voltage. In this case, a bias current may be reduced and a TC input terminal circuit may operate in the low power mode.

Also, an input PMOS transistor included in a transistor 220 of FIG. 2A may be provided in a reconfigurable form. In this case, a W/L ratio of the input PMOS transistor changes to the low power mode and the TC input terminal circuit operates at an optimal operating point.

Each of the transistors illustrated in FIGS. 2 and 3 may be provided in a reconfigurable form. A detailed description of a configuration of a reconfigurable transistor will be provided with reference to FIGS. 5 through 8.

Figure 5A:
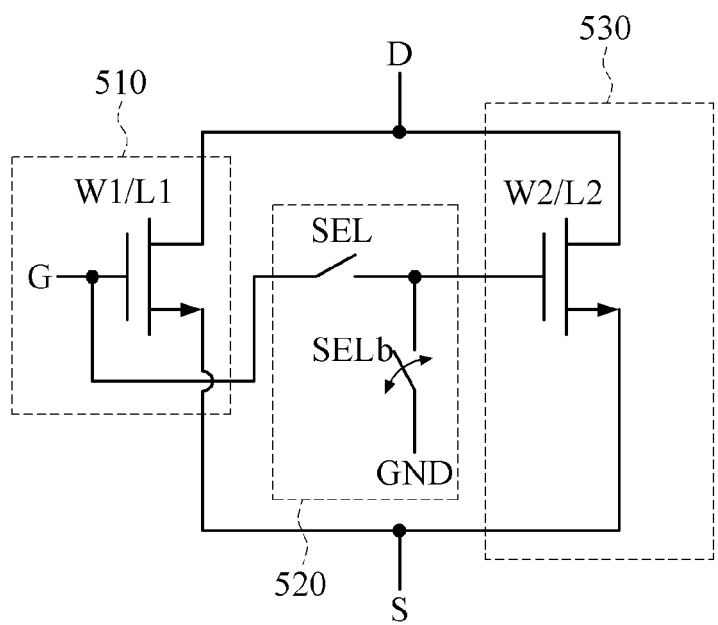
FIG. 5A is a diagram illustrating an example of a switching circuit used to reconfigure a width and a length of an N channel metal oxide semiconductor field effect transistor (MOSFET) (NMOS).
Figure 5B:
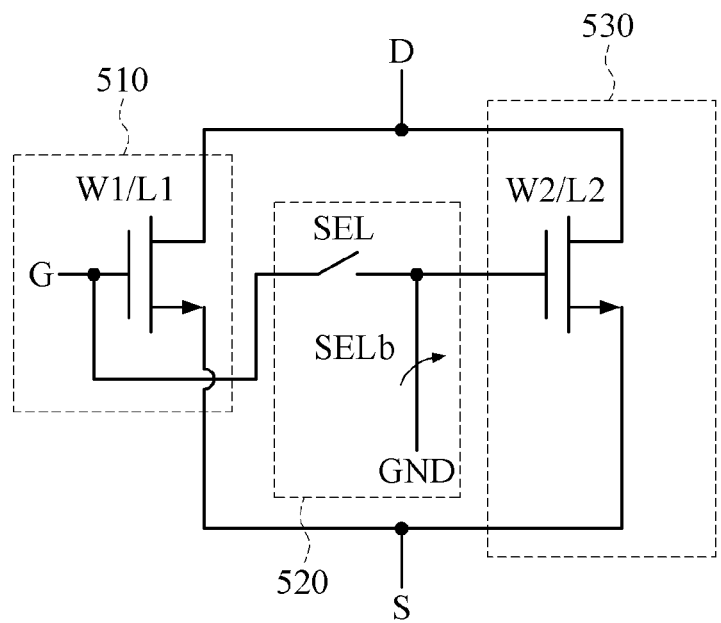
FIG. 5B is a diagram illustrating an example of a switching circuit used to reconfigure a width and a length of an N channel metal oxide semiconductor field effect transistor (MOSFET) (NMOS).

FIG. 5A-5B is a diagram illustrating an example of a switching circuit to reconfigure a width and a length of an N channel metal oxide semiconductor field effect transistor (MOSFET) (NMOS), in accordance with an embodiment. Referring to FIG. 5A, a reconfigurable NMOS transistor may include transistors 510 and 530. The reconfigurable NMOS transistor may be included in a circuit that is configured to adjust the width and the length of the NMOS transistor through gate switching. In one configuration, the reconfigurable NMOS transistor does not include a serial switch on a source-drain path through which a current flows. As a result, a non-ideal characteristic or a nonlinear characteristic caused by the serial switch is eliminated.

For example, as illustrated in FIG. 5B, the W/L of the transistor 510 is shown as W1/L1 and the W/L of the transistor 530 is shown as W2/L2. When operating a transistor having W1/L1, a logic value of "0" is input to a selection signal (SEL) of a gate switching unit 520 and a logic value of "1" is input to a selection signal (SELb). In this case, a gate of the transistor 530 is connected to a ground (GND). The transistor 530 is turned off and the NMOS transistor performs an operation identical to the transistor having W1/L1.

When a logic value of "1" is input to the selection signal (SEL) of the gate switching unit 520 and a logic value of "0" is input to the selection signal (SELb), a gate of the transistor 510 and the gate of the transistor 530 is connected to each other. The transistor 510 and the transistor 530 share a gate signal. The reconfigurable NMOS transistor operates equivalently to a transistor having a width/length indicated as (W1+W2*L1/L2)/(L1). When L1 equals L2, the reconfigurable NMOS transistor is configured to operate as a transistor having a width/length indicated as (W1+W2)/L1.

Figure 6A:
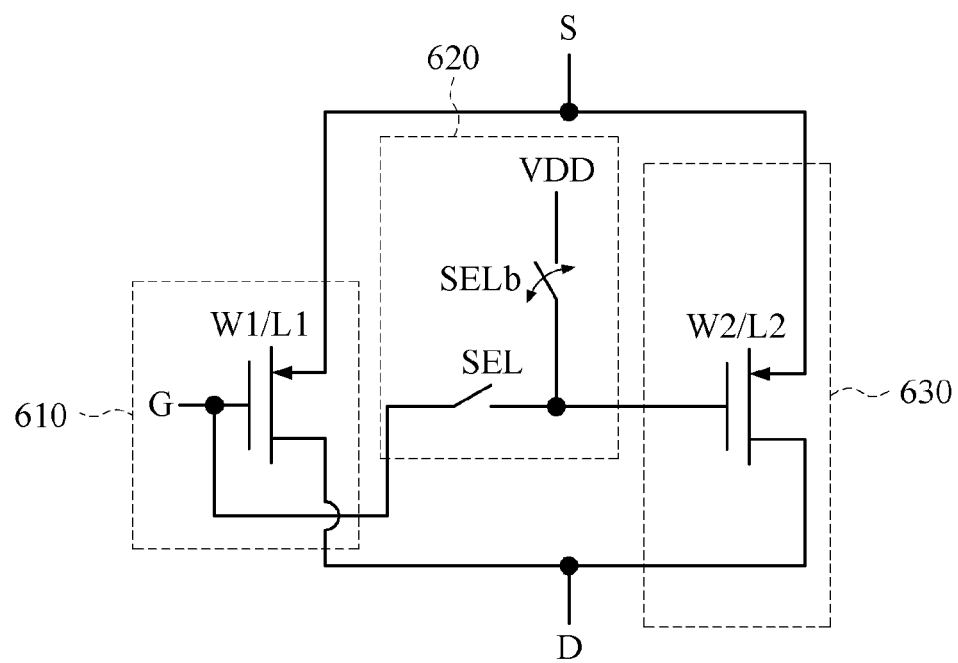
FIG. 6A is a diagram illustrating an example of a switching circuit used to reconfigure a width and a length of a P channel MOSFET (PMOS), in accordance with an embodiment.
Figure 6B:
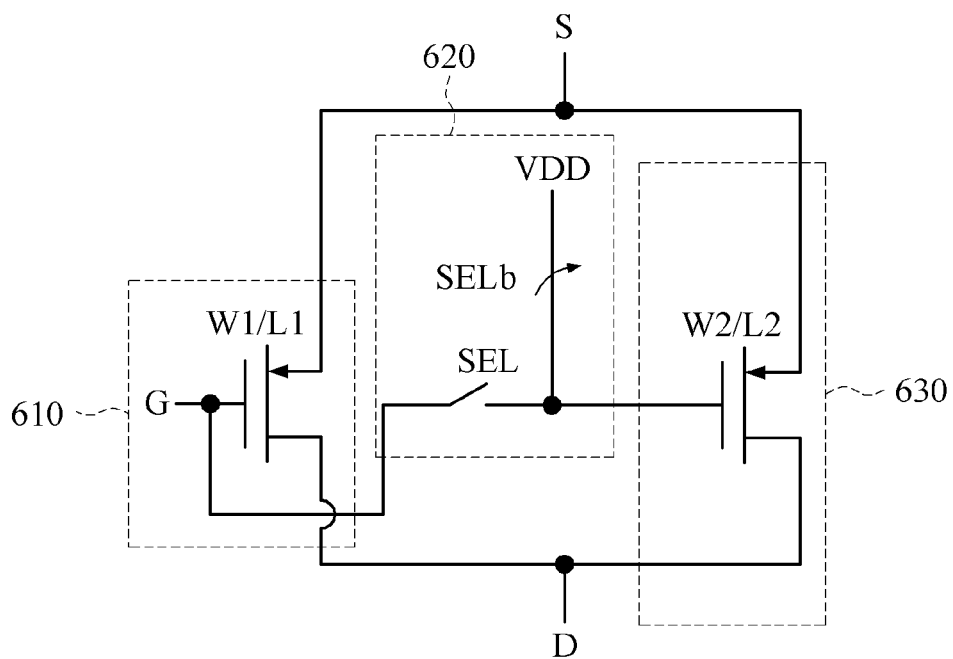
FIG. 6B is a diagram illustrating an example of a switching circuit used to reconfigure a width and a length of a P channel MOSFET (PMOS), in accordance with an embodiment.

FIG. 6A-6B is a diagram illustrating an example of a switching circuit to reconfigure a width and a length of a P channel MOSFET (PMOS), in accordance with an embodiment. Referring to FIG. 6A-6B, a reconfigurable PMOS transistor may be implemented in a manner similar to the reconfigurable NMOS transistor of FIG. 5A-5B. The reconfigurable PMOS transistor includes transistors 610 and 630. The reconfigurable PMOS transistor includes a circuit that is configured to adjust the width and the length of the PMOS transistor through gate switching. In one configuration, the reconfigurable PMOS transistor does not include a serial switch on a source-drain path through which a current flows. As a result, a non-ideal characteristic and a nonlinear characteristic caused by the serial switch may be eliminated.

For example, the W/L of the transistor 610 is indicated as W1/L1 and the W/L of the transistor 630 may be indicated as W2/L2. When operating a transistor having W1/L1, a logic value of "0" is input to a selection signal (SEL) of a gate switching unit 620 and a logic value of "1" is input to a selection signal (SELb). In this case, a gate of the transistor 630 is connected to an operating voltage (VDD). The transistor 630 is turned off, and the reconfigurable PMOS transistor performs operations equivalent to the transistor having W1/L1.

When a logic value of "1" is input to the selection signal (SEL) of the gate switching unit 620 and a logic value of "0" is input to the selection signal (SELb), a gate of the transistor 610 and the gate of the transistor 630 are connected to each other. The transistor 610 and the transistor 630 share a gate signal. The reconfigurable PMOS transistor operates equivalently to a transistor having a W/L indicated as (W1+W2*L1/L2)/(L1). When L1 equals L2, the reconfigurable PMOS transistor is configured to operate as a transistor having a width/length indicated as (W1+W2)/L1.

Figure 7A:
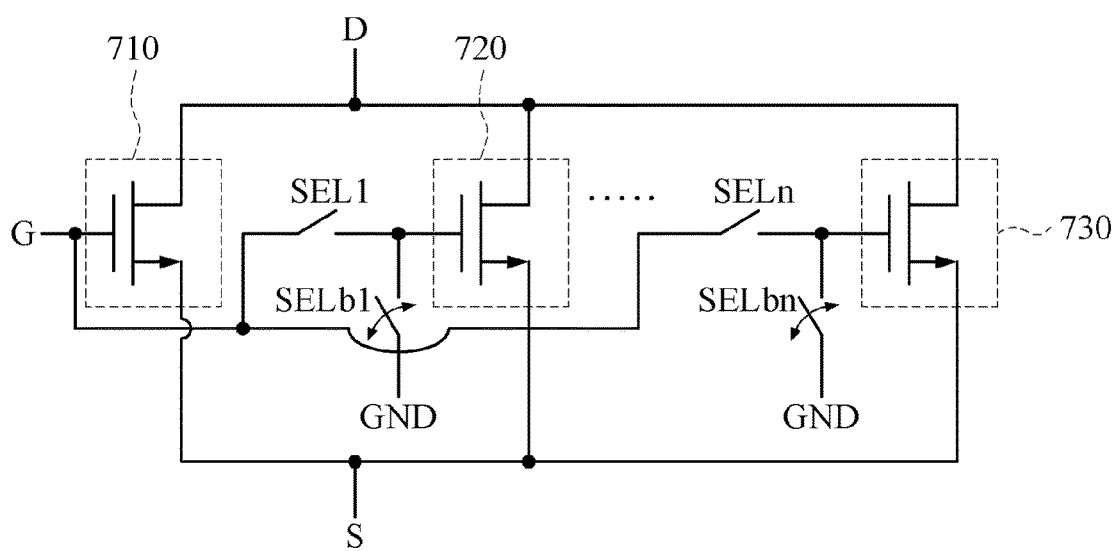
FIG. 7A is a diagram illustrating an example of a switching circuit used to reconfigure a width and a length of an NMOS transistor to multiple levels, in accordance with an embodiment.
Figure 7B:
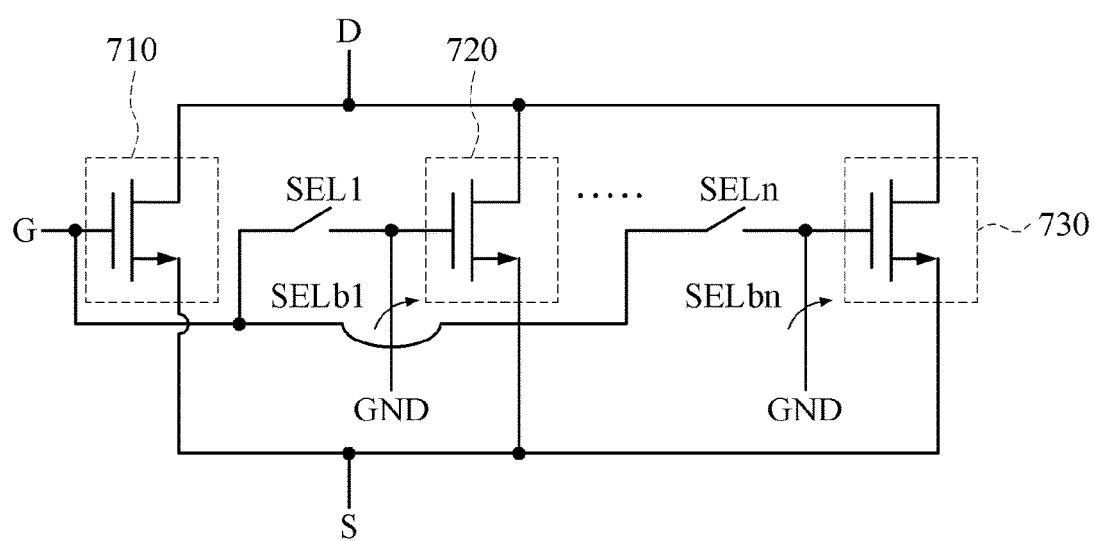
FIG. 7B is a diagram illustrating an example of a switching circuit used to reconfigure a width and a length of an NMOS transistor to multiple levels, in accordance with an embodiment.

FIG. 7A-7B is a diagram illustrating an example of a switching circuit to reconfigure a width and a length of an NMOS transistor to multiple levels, in accordance with an embodiment. Referring to FIG. 7A-7B, the NMOS transistor that is reconfigured to multiple levels may include transistors 710, 720, and 730. The transistors 720 and 730 may each be determined to be on or off based on a signal applied to gates of the transistors 720 and 730 and thus, the width and the length of the NMOS transistor may be reconfigured to the multiple levels.

Figure 8A:
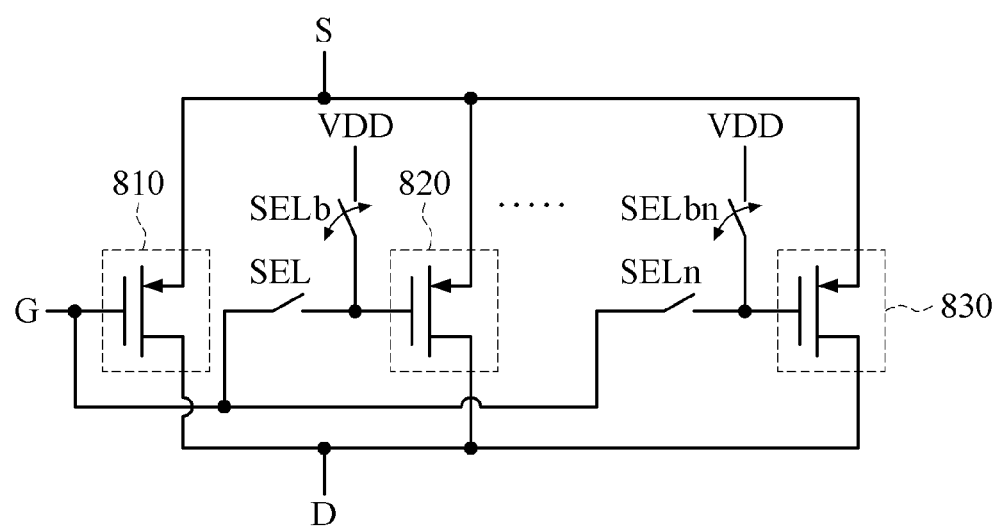
FIG. 8A is a diagram illustrating an example of a switching circuit used to reconfigure a wide and a length of a PMOS transistor to multiple levels, in accordance with an embodiment.
Figure 8B:
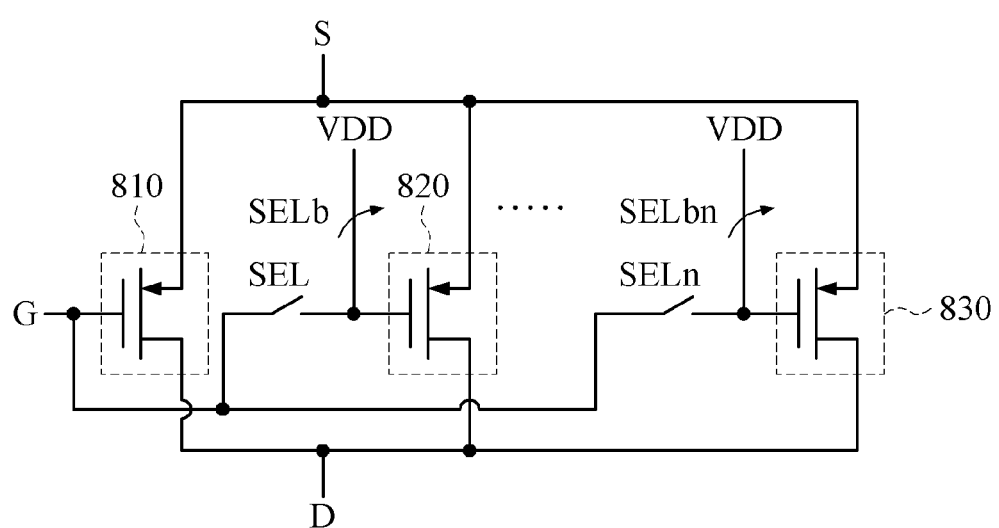
FIG. 8B is a diagram illustrating an example of a switching circuit used to reconfigure a wide and a length of a PMOS transistor to multiple levels, in accordance with an embodiment.

FIG. 8A-8B is a diagram illustrating an example of a switching circuit to reconfigure a W and an L of a PMOS transistor to multiple levels, in accordance with an embodiment. Referring to FIG. 8A-8B, the PMOS transistor is reconfigured to multiple levels and includes transistors 810, 820, and 830. Each of the transistors 820 and 830 is determined to be on or off based on a signal applied to gates of the transistors 820 and 830. As a result, the W and the L of the PMOS transistor is reconfigured to the multiple levels.

Dynamic Switching

A biosignal amplifying circuit may dynamically control a current source provided to an amplification circuit. For example, the biosignal amplifying circuit dynamically controls the current source provided to the amplification circuit at a timing through a transistor being on or off. The biosignal amplifier or amplifying circuit performs sampling and hold of desired signals on nodes at a dynamic current source control timing; thus, reducing an average amount of consumed current. For example, a sample and hold circuit may be applied to an offset elimination loop and a common mode rejection ratio (CMRR) improving circuit. The sample and hold is referred to as "sampling" and a held signal may be referred to as a "sampled signal."

Referring to FIG. 1B and FIG. 1C, the amplifier 120 further includes a sample and hold circuit 140 to perform sampling and hold of an output voltage at the TI output terminal 160 at a suitable timing and another sample and hold circuit 145 to perform sampling and hold of an output voltage at the TC input terminal 150. A DSL 130 feeds the output voltage of the sample and hold circuit 145 back to the TC input terminal 150. Another DSL 135 feeds the output voltage of the sample and hold circuit 140 back to the TC input terminal 150.

The biosignal amplifying circuit further includes a timing generator 190. The timing generator 190 generates an enable signal (EN) that turns on or off a current source of the TC input terminal 150 and the TI output terminal 160 based on an operating timing of a chopper stabilization circuit. A state of the TC input terminal 150 and the TI output terminal 160 changes between an operating state and a low power state based on a control signal that periodically changes, such as an enable signal.

Also, the timing generator 190 generates a sampling signal (SMPL) to sample the output voltage at the TC input terminal 150 and the TI output terminal 160. When the TC input terminal 150 and the TI output terminal 160 are in the operating state, the output signal at the TC input terminal 150 and the TI output terminal 160 is sampled based on, corresponding to, or as a function of the timing of the sampling signal. Also, when the TC input terminal 150 and the TI output terminal 160 are in the low power state, a held signal may be output based on the timing of the sampling signal.

Referring to FIG. 2B, a bias current of the flipped voltage follower 240 is controlled by the switching unit 280. The multiplexer 290 selects bias voltages including voltage (BIAS1) and a voltage (BIAS2). When an enable signal (EN) generated by the timing generator 190 has a logic value of "1," the switching unit 280 provides a bias voltage. Also, when the enable signal (EN) generated by the timing generator 190 has a logic value of "0," the switching unit 280 does not provide a bias voltage. Thus, an amount of current consumption is reduced.

Referring to FIG. 3, switching unit 360 controls the current source of a transistor 350. A voltage (CASN) is a bias voltage selected by a multiplexer. When an enable signal (EN) generated at the timing generator 190 has a logic value of "1," the switching unit 360 provides a bias voltage. Also, when the enable signal (EN) generated at the timing generator 190 has a logic value of "0," the switching unit 360 does not provide a bias voltage. Thus, an amount of current consumption is reduced.

Figure 12:
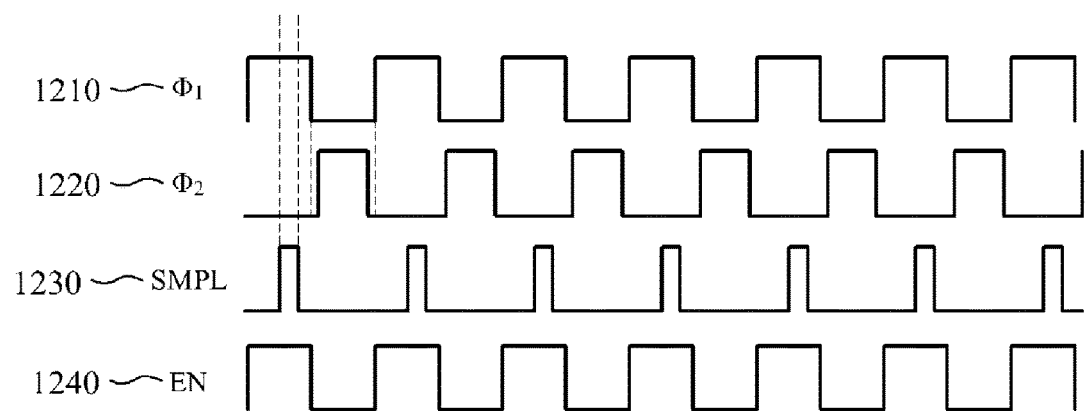
FIGS. 12 and 13 are diagrams illustrating examples of timings of a sampling signal and an enable signal, in accordance with an embodiment.
Figure 13:
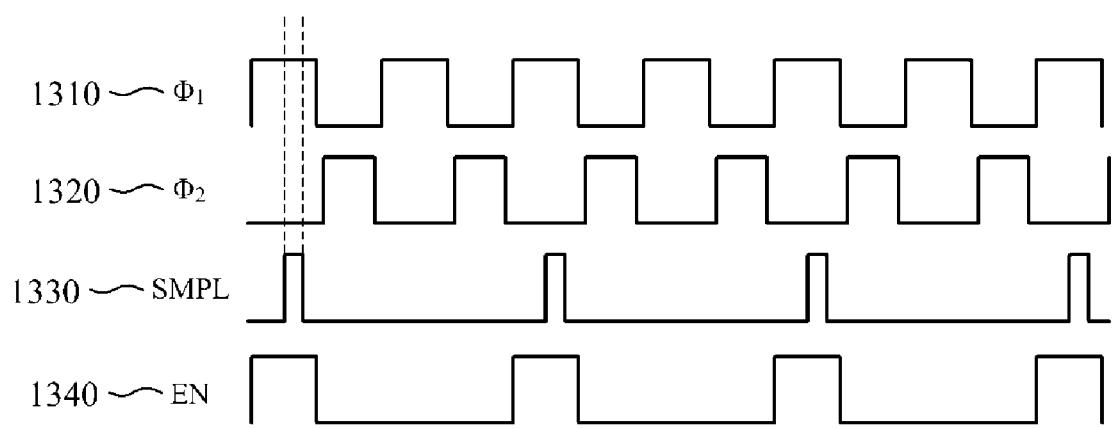

FIGS. 12 and 13 are diagrams illustrating examples of timings of a sampling signal and an enable signal. Referring to FIGS. 12 and 13, an operating timing of a chopper included in the modulation circuit 110 of FIG. 1A is determined based on a first frequency signal ($\Phi 1$) and a second frequency signal ($\Phi 2$).

As described in the foregoing, the TC input terminal 150 and the TI output terminal 160 of FIG. 1B consume power only when the enable signal has a logic value of "1". As a result, an average amount of power consumption is reduced through the enable signal being on or off. As illustrated in FIG. 12, the enable signal is turned on or off in each cycle of a first frequency signal 1210. As illustrated in FIG. 13, the enable signal is turned on or off in every two cycle of a first frequency signal 1310. Thus, the amount of power consumption is further reduced. The examples illustrated in FIGS. 12 and 13 are provided only as illustrative examples and; thus, the descriptions herein are not limited thereto.

Referring to FIG. 1A, a current provided to the TC input terminal 150 is controlled by the enable signal generated by the timing generator 190. In response to the enable signal having a logic value of "1," the TC input terminal 150 normally functions or operates. In response to the enable signal having a logic value of "0," the TC input terminal 150 functions or operates in a low power mode.

In response to the enable signal having a logic value of "1," the TC input terminal 150 and the TI output terminal 160 output a normal signal. In response to the enable signal having a logic value of "0," an output signal of the TC input terminal 150 and an output signal of the TI output terminal 160 may not be the normal signal. Similarly, in response to the enable signal having a logic value of "0," a terminal outputting a common mode voltage (VCM) at the TC input terminal 150 does not output a normal signal.

Thus, when the enable signal has a logic value of "1," the sample and hold circuits 140, 145, and 170 sample and store the normal signal. Switches (SMPL) of the sample and hold circuits 140, 145, and 170 may be controlled by the sampling signals 1230 and 1330 of FIGS. 12 and 13.

For example, in response to the sampling signal having a logic value of "1," the sample and hold circuit 145 samples an output voltage of a terminal (PREP) and an output voltage of a terminal (PREN) of the TC input terminal 150 and stores the sampled voltages in a capacitor. A voltage held in the sample and hold circuit 145 is negatively fed back to a terminal (IFR) and a terminal (IFL) of the TC input terminal 150 through a DSL 130. Thus, a DC offset is eliminated.

An output signal of a terminal (TCOP) and an output signal of a terminal (TCON) of the TC input terminal 150 are transmitted to the TI output terminal 160. The transmitted signal may be demodulated by a timing of a chopper stabilization circuit and output to a terminal (IA_ON) and a terminal (IA_OP). The output signal is sampled and held by the sample and hold circuit 140 and output to a terminal (OUTN) and a terminal (OUTP). Also, the held signal is negatively fed back to a terminal (OFR) and a terminal (OFL) of the TI input terminal 150 through a DSL 135. Thus, a DC offset is eliminated.

A common mode signal output from a terminal (VCM) of the TC input terminal 150 is sampled and held at the sample and hold circuit 170. The held signal may be amplified through the bootstrap circuit 175. The amplified signal may be positively fed back to input terminals (INP and INN) of the modulation circuit 110. As a result, input impedance of the input terminals (INP and INN) increase and a CMRR is improved.

A voltage held in the sample and hold circuit 170 is negatively fed back to a shield signal of a cable connecting a human body to a circuit and to a human body through the driven right leg (DRL) circuit 180.

Implementation of a Low Noise Characteristic

A biosignal amplifying circuit reduces 1/f noise and obtains a low noise characteristic. The 1/f noise is referred to as flicker noise which is a unique noise generated from an active device. When noise generated from an internal side of the active device is indicated on an axis of frequency, an amplitude of the noise increases in a low frequency band, for example, less than or equal to 100 hertz (Hz). The magnitude of the 1/f noise increases in inverse proportion to the frequency.

The biosignal amplifying circuit reduces the 1/f noise by applying both a large signal excitation (LSE) method and a chopper stabilization method. When the LSE method is applied at an identical power consumption level and an identical thermal noise level, 1/f corner may be reduced and, as a result, the 1/f noise may be effectively avoided at a low carrier frequency of a copper.

Referring to FIG. 2A, the transistor 220 and the transistor 230 are configured to be a pair of input PMOS transistors at a TC input terminal. Each of the input PMOS transistors may be implemented by the LSE method.

Figure 9:
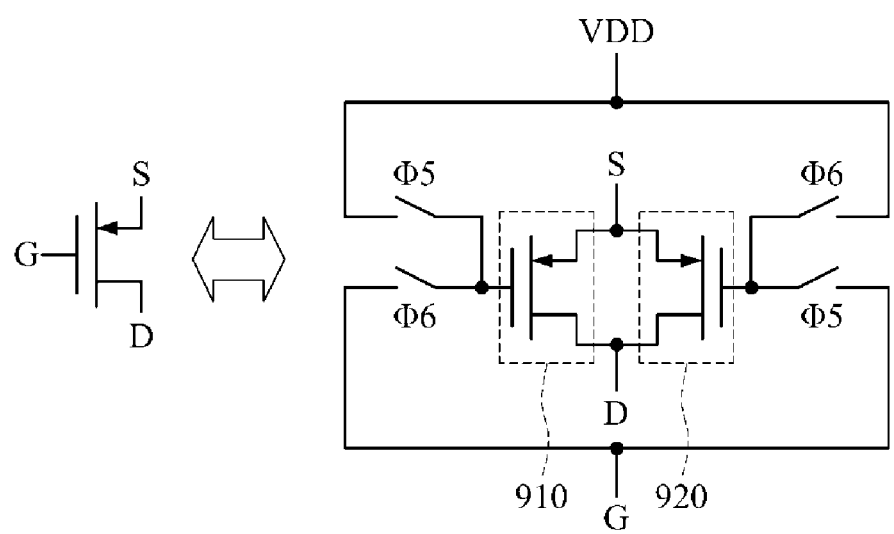
FIG. 9 is a diagram illustrating an example of a noise reducing circuit for a PMOS transistor, in accordance with an embodiment.

FIG. 9 is a diagram illustrating an example of a noise reducing circuit for a PMOS transistor, in accordance with an embodiment. Referring to FIG. 9, one PMOS transistor includes two transistors 910 and 920 and four switches. The four switches may operate by a clock of a fifth frequency signal ($\Phi 5$) and a sixth frequency signal ($\Phi 6$). Respective sources and drains of the two transistors 910 and 920 are connected to one another. Respective gates of the two transistors 910 and 920 are connected to a switch.

Figure 14:
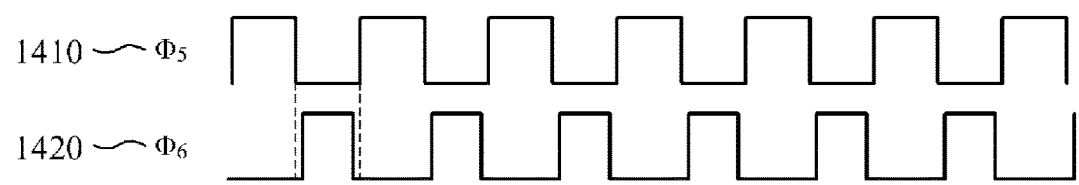
FIG. 14 is a diagram illustrating an example of a timing of a switching control signal of a noise reducing circuit, in accordance with an embodiment.

FIG. 14 is a diagram illustrating an example of a timing of a switching control signal of a noise reducing circuit, in accordance with an embodiment. Referring to FIG. 14, a fifth frequency signal ($\Phi 5$) and a sixth frequency signal ($\Phi 6$) are configured as a non-overlapping clock.

Referring back to FIG. 9, one of the two transistors 910 and 920 is turned on based on the fifth frequency signal ($\Phi 5$) and the sixth frequency signal ($\Phi 6$) and the other of the two transistors 910 and 920 is turned off and, as a result, the two transistors 910 and 920 may equivalently operate as a single transistor.

Figure 10:
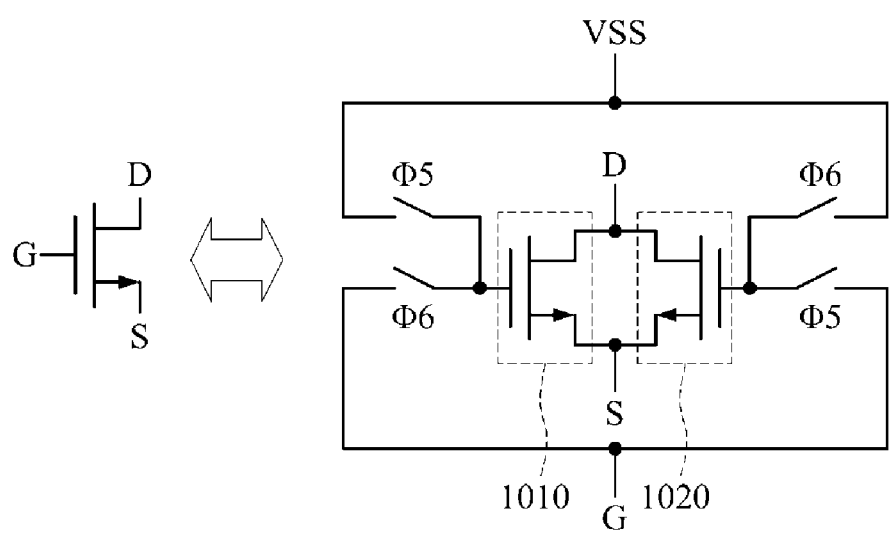
FIG. 10 is a diagram illustrating an example of a noise reducing circuit for an NMOS transistor, in accordance with an embodiment.

FIG. 10 is a diagram illustrating an example of a noise reducing circuit for an NMOS transistor, in accordance with an embodiment. Referring to FIG. 10, one NMOS transistor includes two transistors 1010 and 1020 and four switches. The four switches operate using a clock of a fifth frequency signal ($\Phi 5$) and a sixth frequency signal ($\Phi 6$). Respective sources and drains of the two transistors 1010 and 1020 are connected to one another. Respective gates of the two transistors 1010 and 1020 are connected to a switch.

One of the two transistors 1010 and 1020 is turned on based on the fifth frequency signal ($\Phi 5$) and the sixth frequency signal ($\Phi 6$) and the remaining one of the two transistors 1010 and 1020 is turned off. As a result, the two transistors 1010 and 1020 may equivalently operate as a single transistor.

A transistor circuit based on the LSE method of FIGS. 9 and 10 may be applied along with a reconfigurable transistor circuit of FIGS. 5 through 8.

Figure 11:
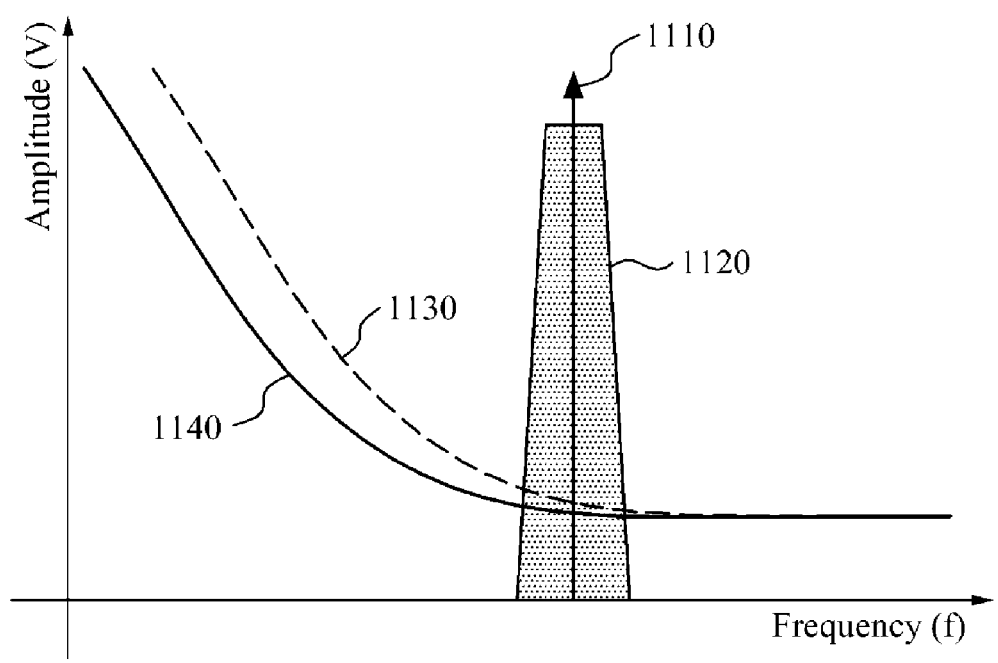
FIG. 11 is a graph illustrating an example of an effect of a noise reducing circuit, in accordance with an embodiment.

FIG. 11 is a graph displaying an example of an effect of a noise reducing circuit, in accordance with an embodiment. Referring to FIG. 11, a signal to noise ratio (SNR) of a signal 1120 modulated at a carrier frequency 1110 of a chopper is affected, for example, by the following noise relationship 1/f. When an LSE method is applied at an identical power consumption level and an identical thermal noise level, 1/f corner may decrease from 1130 to 1140 and; thus, the 1/f noise is effectively avoided at a low carrier frequency of the chopper.

Figure 15:
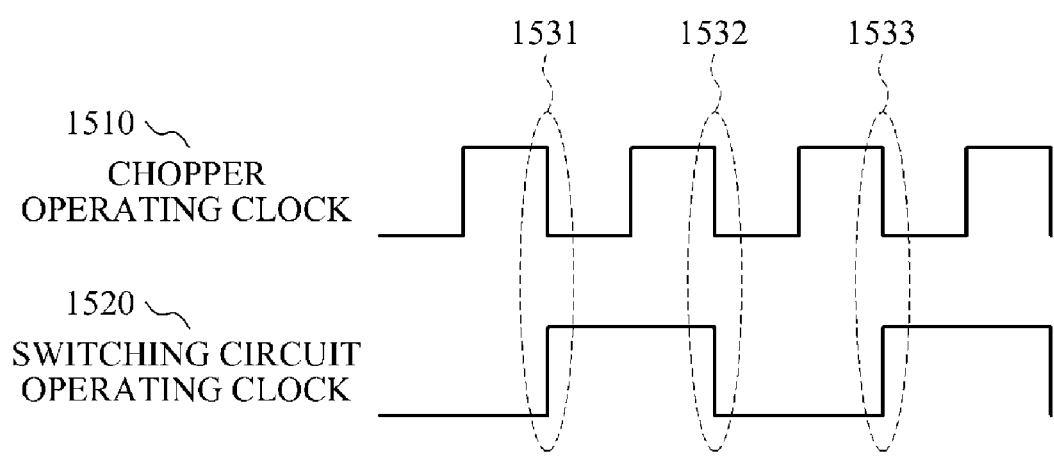
FIGS. 15 and 16 are diagrams illustrating examples of synchronization of a chopper operating clock and a switch circuit operating clock, in accordance with an embodiment.
Figure 16:
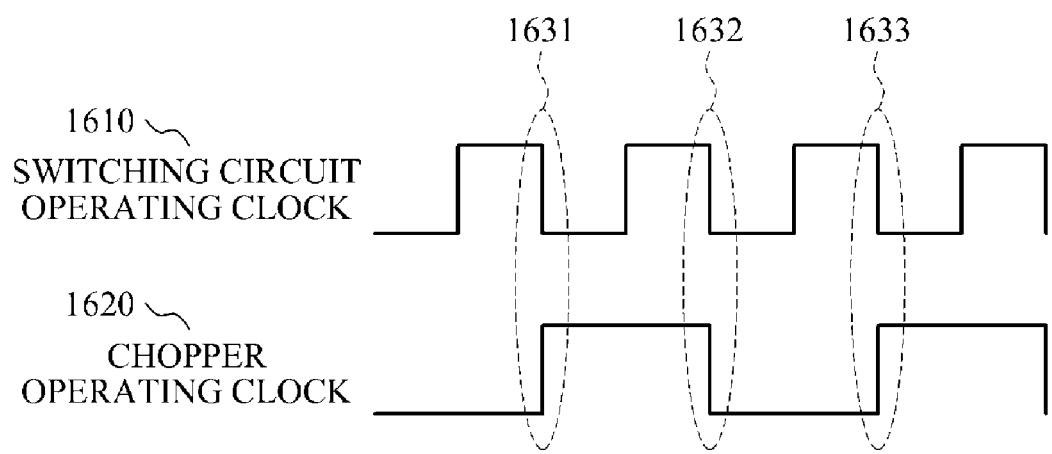

FIGS. 15 and 16 are diagrams illustrating examples of synchronization of a chopper operating clock and a switching circuit operating clock, in accordance with an embodiment. Referring to FIG. 15, an edge of a chopper operating clock 1510 and an edge of a switching circuit operating clock 1520 are synchronized. The chopper operating clock 1510 refers to a clock operating a chopper included in the modulation circuit 110 of FIG. 1A. Also, the chopper operating clock 1510 refers to a clock operating the chopper 320 and the chopper 340 of FIG. 3. The switching circuit operating clock 1520 refers to a clock operating the switching circuit of FIG. 9 and the switching circuit of FIG. 10.

For example, the switching circuit operating clock 1520 is synchronized with a falling edge of the chopper operating clock 1510. The falling edge of the chopper operating clock 1510 and a rising edge of the switching circuit operating clock 1520 is synchronized at a timing 1531. The falling edge of the chopper operating clock 1510 and a falling edge of the switching circuit operating clock 1520 are synchronized at a timing 1532. Similarly, the falling edge of the chopper operating clock 1510 and the rising edge of the switching circuit operating clock 1520 are synchronized at a timing 1533.

Referring to FIG. 16, an edge of a chopper operating clock 1620 and an edge of a switching circuit operating clock 1610 are synchronized. The chopper operating clock 1620 refers to a clock operating a chopper included in the modulation circuit 110 of FIG. 1A. The chopper operating clock 1620 refers to a clock operating the chopper 320 and the chopper 340 of FIG. 3. The switching circuit operating clock 1610 refers to a clock operating the switching circuit of FIG. 9 or the switching circuit of FIG. 10.

For example, the chopper operating clock 1620 is synchronized with a falling edge of the switching circuit operating clock 1610. The falling edge of the switching circuit operating clock 1610 and a rising edge of the chopper operating clock 1620 are synchronized at a timing 1631. The falling edge of the switching circuit operating clock 1610 and a falling edge of the chopper operating clock 1620 are synchronized at a timing 1632. Similarly, the falling edge of the switching circuit operating clock 1610 and the rising edge of the chopper operating clock 1620 are synchronized at a timing 1633.

According to examples described herein, various structural and functional configurations are provided to control power consumption of a circuit by multiplexing a current source and a voltage source. According to the various examples described herein, various structural and functional configurations are provided to respond to a change in an operating point using a transistor circuit configured to reconfigure a width and a length when multiplexing a current source and a voltage source.

According to various examples described herein, various structural and functional configurations are described to reduce an average amount of consumed power by controlling a dynamic current source based on a chopper stabilization method. According to various examples described herein, various structural and functional configurations are described to eliminate a DC offset using a desirable sample and hold circuit when controlling a dynamic current source and improving a CMRR.

For example, an amount of consumed power is reduced through static switching and dynamic switching at a low power mode, and a DSL method and/or a common mode signal feedback method may be applied.

According to various examples described herein, various structural and functional configurations are described to effectively avoid low frequency noise by applying both a chopper stabilization method and an LSE method. For example, the chopper stabilization method and the LSE method may be applied together to avoid the low frequency noise in a high quality mode.

According to various examples described herein, various structural and functional configurations are described to provide an instrumentation amplifier to measure a biosignal that reconfigures power consumption, an operating point, and a gain and output a high quality signal from which a DC offset is eliminated and include an improved CMRR. According to various examples described herein, an instrumentation amplifier to measure a biosignal that is reconfigurable and flexible and of low power and high performance are implemented, which may be applicable to, for example, measure an electrocardiogram (ECG) and a brain wave.

The units described herein may be implemented using hardware components. For example, the hardware components may include microphones, switches, amplifiers, bandpass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

It is to be understood that in the embodiment described above, the operations of the methods described above performed in the sequence and manner as described although the order of some operations and the like may be changed without departing from the spirit and scope of the described configurations. In accordance with an illustrative example, a computer program embodied on a non-transitory computer-readable medium may also be provided, encoding instructions to perform at least the chopper stabilization method, the DSL method, the common mode signal feedback method, and the LSE method, for example, described above.

Program instructions to perform the methods described above, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein may be easily construed by programmers skilled in the art to which the embodiments pertain based on and using the flow diagrams and block diagrams of the figures and their corresponding descriptions as provided herein.

As a non-exhaustive illustration only, a terminal or device described herein may refer to mobile devices such as a cellular phone, a personal digital assistant (PDA), a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biosignal apparatus, comprising:
    an amplifier configured to alternate between an operating state and a low power state based on a periodically changing control signal; and
    a sampler configured to sample a signal output from the amplifier in response to the amplifier being in the operating state and to maintain the sampled signal in response to the amplifier being in the low power state,
    wherein the amplifier is further configured to receive an enable signal and to receive a bias voltage to amplify an input signal in response to the enable signal having a logic value corresponding to the operating state, and
    wherein a period length of the enable signal is greater by a factor of a period length of the control signal.

2. The apparatus of claim 1, further comprising:
    a selector configured to select the bias voltage corresponding to the operating mode, wherein the amplifier comprises switches to be reconfigured based on an operating point corresponding to the operating mode.

3. The apparatus of claim 2, wherein each of the switches comprises transistors sharing a source and a drain,
    wherein the transistors are configured to receive an identical gate signal at a first operating point, and
    wherein at least a part of the transistors is configured to receive a gate signal that turns off the part of the transistors at a second operating point.

4. The apparatus of claim 1, wherein the amplifier comprises a switch comprising transistors to be alternately turned on and off.

5. The apparatus of claim 4, wherein the switch comprises two transistors sharing a source and a drain,
    wherein, at a first timing, a gate of a first transistor is configured to receive a gate signal and a second transistor is configured to be turned off, and
    wherein, at a second timing, a gate of the second transistor is configured to receive the gate signal and the first transistor is turned off.

6. The apparatus of claim 1, wherein the sampler is disposed at an input terminal of a direct current servo loop (DSL) circuit.

7. The apparatus of claim 1, wherein the sampler is disposed at an input terminal of a bootstrap circuit.

8. The apparatus of claim 1, wherein the amplifier further comprises:
    a transconductance (TC) input terminal configured to convert and amplify a modulated input voltage to a current; and
    a transimpedance (TI) output terminal configured to convert and amplify an input current to an output voltage.

9. The apparatus of claim 8, further comprising:
    a timing generator configured to generate the enable signal (EN) that turns on or off a current source of the TC input terminal and the TI output terminal based on an operating timing of a chopper stabilization device, and configured to sample the output voltage.

10. The apparatus of claim 1, wherein a selector selects a bias current source by multiplexing a current source and a voltage source to reconfigure an amount of power consumption.

11. A biosignal apparatus, comprising:
    a switch configured to be reconfigured based on an operating point of an operating mode; and
    a selector configured to select a bias voltage corresponding to the operating mode, wherein the switch comprises transistors sharing a source and a drain,
    wherein, at a first operating point, the transistors are configured to receive an identical gate signal, and
    wherein, at a second operating point, at least a part of the transistors is configured to receive a gate signal that turns off the part of the transistors.

12. The apparatus of claim 11, wherein a width and a length of the switch is reconfigured based on the operating point.

13. The apparatus of claim 11, wherein the operating mode comprises a low power mode and a high quality mode.

14. The apparatus of claim 11, wherein through static switching, the selector selects a bias current source by using a multiplexing scheme to reconfigure an amount of power consumption.

15. A biosignal apparatus, comprising:
    a switch comprising transistors;
    a controller configured to control the switch to enable the transistors to be alternately turned on and off;
    a modulator configured to modulate an input signal to a high frequency; and
    a demodulator configured to demodulate the modulated signal,
    wherein an edge of a clock operating a chopper in the modulator and a chopper in the demodulator and an edge of a clock operating the switch are periodically synchronized.

16. The apparatus of claim 15, wherein the switch comprises two transistors sharing a source and a drain,
    wherein, at a first timing, a gate of a first transistor is configured to receive a gate signal and a second transistor is configured to be turned off, and
    wherein, at a second timing, a gate of the second transistor is configured to receive the gate signal and the first transistor is turned off.

17. The apparatus of claim 15, wherein the switch is disposed at an input terminal of the biosignal apparatus.

\* \* \* \* \*